United States Patent [19]

Schmolka

[11] Patent Number: 4,495,168

[45] Date of Patent: Jan. 22, 1985

[54] AEROSOL GEL

[75] Inventor: Irving R. Schmolka, Grosse Ile, Mich.

[73] Assignee: BASF Wyandotte Corporation, Wyandotte, Mich.

[21] Appl. No.: 525,148

[22] Filed: Aug. 22, 1983

[51] Int. Cl.³ .................. A61K 7/00; A61K 7/15; A61L 9/04
[52] U.S. Cl. .................................. 424/45; 424/47; 424/73; 424/DIG. 13; 424/78
[58] Field of Search .............. 424/45, 47, 73, 78, 424/DIG. 13; 222/4, 394, 402.1

[56] References Cited

U.S. PATENT DOCUMENTS

| | | | |
|---|---|---|---|
| 3,476,853 | 11/1969 | Jatul et al. | 424/45 |
| 3,639,575 | 2/1972 | Schmolka | 424/DIG. 13 X |
| 3,740,421 | 6/1973 | Schmolka | 424/65 |
| 3,751,562 | 8/1973 | Nichols | 424/45 |
| 4,001,391 | 1/1977 | Feinstone et al. | 424/45 |
| 4,293,542 | 10/1981 | Lang et al. | 424/47 |
| 4,360,451 | 11/1982 | Schmolka | 252/316 |
| 4,376,764 | 3/1983 | Schmolka | 424/78 |

FOREIGN PATENT DOCUMENTS 1444334 7/1976 United Kingdom .

*Primary Examiner*—Sidney Marantz
*Assistant Examiner*—Shawn P. Foley
*Attorney, Agent, or Firm*—Bernhard R. Swick

[57] ABSTRACT

A pressurized composition in an aerosol container and adapted to form a spray upon release of pressure therefrom which composition is a liquid inside the container and forms a gel on contact with living tissue comprising water, propellant and a polyoxyethylene-polyoxybutylene copolymer. The preferred composition also includes a volatile solvent and may advantageously include a skin treating agent, and conventional adjuvants.

15 Claims, No Drawings

AEROSOL GEL

BACKGROUND OF THE INVENTION

1. Field of the Invention

The present invention relates to a sprayable aerosol composition which is a liquid in the aerosol container and forms a gel upon application to the skin.

2. Prior Art

The preparation of aqueous gels employing as gelling agents polyoxyalkylene block copolymers is well known to those skilled in the art and is taught in several patents including U.S. Pat. No. 3,740,421.

The use of polyoxybutylene-polyoxyethylene block copolymers in the preparation of aqueous gels is known to those skilled in the art. More specifically, U.S. Pat. No. 4,343,785 discloses a gel dentifrice containing such block copolymers.

U.S. Pat. No. 3,751,562, issued Aug. 7, 1973, to Nichols, discloses an aerosol gel formulation employing an oxyethylated fatty alcohol, mineral oil, iodine and water.

U.S. Pat. No. 4,293,542, issued Oct. 6, 1981, to Lang et al, discloses aerosol formulations which can be an aqueous gel containing oxyethylated fatty alcohols and a gel-forming agent and, as an essential component, a pyridine derivative.

It is known in the art to apply such compositions by the use of aerosol-type containers. However, filling an aerosol container with a gel presents problems.

British Pat. No. 1,096,357 discloses an aerosol gel comprising a partial fatty acid soap of a polyvalent metal hydroxide, a nonpolar oil along with propellants.

The treatment of burns with medicated liquid such as silver ion solutions is well known in the art as evidenced by Moyer et al, *Arch, Surg.* 90, June, 1965. Briefly, the known treatments of burns comprise applying a solution of medication such as a silver nitrate solution to a burn wound. Because this treatment involves liquid solutions, it is known as a wet dressing method. The conventional wet dressing method suffers from many disadvantages. Some of these include (1) exacerbation of the hypermetabolic state by increasing caloric deficit and heat loss, (2) loss of plasma water, serum protein, and serum electrolytes, (3) maceration of burn wound surfaces, (4) increase of fluid loss by vaporization, (5) extensive nursing care, (6) economic loss due to discoloration of bedding, equipment, floors and walls. With so many disadvantages, it is not surprising that the art has searched for an alternate method of treating burns.

In U.S. Pat. No. 3,476,853, a sprayable composition for use as a dressing including a film-forming material, an opacifying material, at least one medicament, a solvent and a gaseous propellant is disclosed. The fluid dressing or bandage is applied by spraying the fluid dressing from a closed pressure-resistant container by the expansion of a normally gaseous propellant in liquid state. The patent discloses a means for applying a protective opaque film which is immediately dry to the touch when applied from a distance of 4 to 6 inches. This provides a simulated bandage.

U.S. Pat. No. 3,639,575 discloses compositions prepared from aqueous gels of polyoxyethylene-polyoxypropylene block copolymers as a matrix for silver ions for burn treatment. There is no disclosure of spraying from an aerosol container.

U.S. Pat. No. 4,376,764 discloses silver ion gel compositions containing a polyoxybutylene-polyoxyethylene block copolymer. These gel compositions may be used to treat burn wounds and superficial ulcers.

British Pat. No. 1,444,334 discloses an aerosol gel composition which may be employed as a shaving cream and which contains as a gelling agent a polyoxypropylene-polyoxyethylene block copolymer. An essential component of the composition is a water-soluble soap. This patent is concerned with the problem of expelling a gel from an aerosol container and particularly avoiding cavitation around the dip tube. Accordingly, the compressed gas or liquified gaseous propellant is required to be substantially insoluble in the gel so that it can act in the manner of a piston to force the gel from the container without cavitation.

Co-pending U.S. patent applications Ser. Nos. 513,439, 525,147, and 524,985 disclose aerosol gel compositions which are liquid in the aerosol can and form a gel upon application to the skin.

SUMMARY OF THE INVENTION

The filling problems inherent in the use of gels in aerosol containers and the cavitation problem discussed in British Pat. No. 1,444,334 are overcome in accordance with the instant invention by the use of a pressurized composition which may be sprayed from an aerosol container and which is liquid inside the container and forms a gel on contact with living tissue such as the skin of a burn victim or in the topical application of cosmetics, pharmaceuticals, shaving creams, etc. This is accomplished by the combination of water, propellant, volatile solvent and certain polyoxyethylene-polyoxybutylene block copolymers. As employed throughout the instant specification and claims, the term "solvent" means a solvent for the gel composition of this invention. The composition may contain at least one skin treating agent, such as cosmetics, pharmaceuticals, and shaving cream components, burn treatment agents, etc., in an effective amount.

The polyoxyethylene-polyoxybutylene block copolymer has a polyoxybutylene hydrophobe molecular weight of about 1000 to 20,000 and the oxyethylene groups constitute 60 to 90 percent of the total weight of the copolymer.

DESCRIPTION OF THE PREFERRED EMBODIMENTS

The aerosol composition of the instant invention comprises by weight about 35 to 80 percent water, about 3 to 50 percent propellant, about 10 to 25 percent of the polyoxyethylene-polyoxybutylene copolymer, 0 to about 10 percent, preferably about 0.05 to 5 percent, of a skin treatment agent, 0 to about 20 percent, preferably about 1 to 10 percent, of a non-propellant volatile solvent, and 0 to about 20 percent, preferably about 1 to 10 percent adjuvants. By the use of a propellant which is also a solvent, the need for a non-propellant solvent is eliminated.

The preferred polyoxybutylene-polyoxyethylene block copolymer of use in the invention is a cogeneric mixture of conjugated polyoxybutylene polyoxyethylene compounds having as a hydrophobe, a polyoxybutylene polymer having a molecular weight of about 1000 to 20,000. The polyoxybutylene compounds are prepared by first condensing butylene oxide with an organic compound containing a plurality of reactive hydrogen atoms to prepare a polyoxybutylene polymer having a molecular weight of about 1000 to 20,000 and subsequently condensing ethylene oxide therewith. The compounds used in this invention conform to the following general formula:

$$Y[(C_4H_8O)_n\text{—}E\text{—}H]_x \quad (A)$$

wherein Y is the residue of a water soluble organic compound containing therein x active hydrogen atoms; n is an integer; x is an integer greater than 1; the values of n and x are such that the molecular weight of the compound, exclusive of E, is about 1000 to 20,000 as determined by hydroxyl number; E is a polyoxyalkylene chain wherein the oxygen/carbon atom ratio is at least 0.5, and E constitutes 60 to 90 percent of the total weight of the compound.

The polyoxybutylene polymer, which is an intermediate in the preparation of the compounds of use in this invention, has the following structure:

$$Y[(C_4H_8O)_nH]_x \quad (B)$$

wherein Y, n and x are defined as in Formula A above.

The preferred compounds of use in this invention are prepared by condensing ethylene oxide in an amount between 60 and 90 percent of the total weight of the resultant compound, with the polyoxybutylene polymer. These compounds have the following formula:

$$Y[(C_4H_8O)_n(C_2H_4O)_mH]_x \quad (C)$$

wherein Y, n and x are defined as in Formula A and m has a value such that the oxyethylene groups constitute about 60 to 90 percent of the total weight of the compound.

When ethylene oxide is condensed with a polyoxybutylene glycol of about 1000 to 20,000 and preferably 2000 to 10,000 molecular weight and derived from a butanediol initiator, the resulting compounds have the following structure:

$$HO(C_2H_4O)_m(C_4H_8O)_n(C_2H_4O)_mH \quad (D)$$

where n is defined as set forth with respect to formula A and m has a value such that oxyethylene groups constitute 60 to 90 percent of the total weight of the compound.

The hydrophilic portion of the polyoxyalkylene compounds may be supplied in whole or in part by other polyoxyalkylene chains in lieu of the polyoxyethylene chain set forth in Formula C. Any polyoxyalkylene chain may be used provided that the oxygen/carbon atom ratio is at least 0.5.

Examples of a water-soluble organic compound containing therein x active hydrogen atoms, the residue of which is Y, are the initiators which may include water, diols such as propane diol, butanediol, triols such as glycerol and trimethylol propane, tetrols such as pentaerythritol as well as initiators containing more than four hydroxyl groups such as hexitol or sucrose. Also, amines and other low molecular weight water-soluble compounds having two or more active hydrogen atoms, such as ethylene diamine or diethylene triamine, may be used as the initiator. Preferably used is butanediol. More preferably used is 1,4-butanediol.

The butylene oxide used in making the hydrophobic polyoxybutylene polymer, which is an intermediate in the preparation of the compounds used in this invention, may be replaced with up to 30 percent by weight of propylene oxide or ethylene oxide when added as a mixture with the butylene oxide. Also, up to 30 percent by weight of propylene oxide or butylene oxide may be used to replace ethylene oxide, when added as a mixture with ethylene oxide, in preparing the surfactants used in this invention. In lieu of butylene oxide, other 4-carbon cyclic ethers such as methyloxetane, tetrahydrofuran and isobutylene oxide may be used.

Surfactants of the invention, conforming to structures C and D above, are those surfactants which have a hydrophobe molecular weight of between about 1000 and 20,000 and ethylene oxide groups in amount of from about 60 to 90 percent of the total weight of the surfactant. Preferably used is a surfactant having a hydrophobe molecular weight of about 2000 to 10,000.

A composition which is a liquid inside the container and forms a gel on contact with living tissue is achieved by including a volatile solvent in the composition. Suitable solvents include alcohols such as methyl, ethyl and propyl, ketones such as acetone, ethers such as methyl, ethyl, methyl-ethyl, and similar ethers, and chlorinated alkanes such as dichloromethane. A non-volatile solvent such as liquid polyethylene glycols, propylene glycol, dipropylene glycol, etc., can be used together with a volatile solvent, provided the mixture is homogeneous.

The propellants can be any one or a blend of the following as examples: propane, isobutane and other petroleum distillates, nitrogen, carbon dioxide, dimethylether, ethylmethylether, methylene chloride, vinyl chloride and fluorochlorohydrocarbons. The latter include Freon 115 pentafluorochloroethane and Freon C-318, octafluorocyclobutane. Where the composition is soluble in the propellant, or where the propellant is soluble in the composition, a non-propellant, volatile solvent may not be needed. Such volatile solvent propellants include dimethyl ether, methylethyl ether and methylene chloride.

Other components of the gel composition of the instant invention would depend on the use of the gel. In many cases it would contain at least one skin treating agent which when included would generally be in an amount of about 0.05 to 10 percent by weight. For a shaving cream application the polyoxyethylene-polyoxybutylene block copolymer may serve as the agent for wetting the chin and the beard whereby an additional agent would not be needed. If a high-foaming oxyalkylene copolymer as described above is selected which has a molecular weight of the polyoxybutylene hydrophobe of about 1000 to 2000 and an amount of oxyethylene groups of 65 to 85 percent of the total copolymer weight, it alone could serve as the foaming agent. The shaving cream may also contain small amounts of conventional beard softening agents and conventional foaming agents well known to those skilled in the art such as nonionic, amphoteric and anionic surfactants. The nonionics could include high foaming ethylene oxide adducts such as fatty alcohol ethoxylates. The anionics could include sodium or potassium lauryl sulfates and lauryl ether sulfates. Other examples of such agents are triethanolamine lauryl sulfate, sodium dodecyl benzene sulfonate, water-soluble polyoxyethylene ethers of alkyl-substituted phenols, amine oxides and phosphate ester based surfactants. Numerous anionic and nonionic wetting agents suitable for the purposes of the present invention are described in detail in McCutcheon's *"Emulsifiers and Detergents,"* 1982.

When designed for treating burns or skin abrasions the aerosol gel composition may contain any water-soluble or water-insoluble salt as well as other drugs conventionally used for treatment of burns or abrasions. Suitable salts would include the nitrates, lactates, acetates, sulfadiazine and other salts of silver or other heavy metals. Antibiotics may also be used such as bacitracin, neomycin, erythromycin, streptomycin, paramycin, bacteriostats such as garamycin, wound healing agents such as piracetem, aloe vera, and other compositions and compounds normally used to speed up burn healing. In general, the composition would contain from about 0.05 to 5 percent by weight of the burn treatment medication.

While a medicament is often useful, protection of the burn or wound can be accomplished without the inclusion of a medicating agent since the gel when used for burn applications projects the burn or wound by itself.

Many and various adjuvants are generally also included in these gels depending on the application for the gel. Other components could include proteins, amino acids, electrolytes and other ingredients normally found in body fluids. Humectants, such as propylene glycol or glycerin, may also be included. Further adjuvants could include silicone oils. Also, other adjuvants which impart further desired qualities to the skin may be incorporated in the compositions of the invention, e.g., skin fresheners or lather stabilizers or the like such as lanolin or its derivatives, lecithin, higher alcohols, dipelargonate ethers or esters, coconut oil and other fatty esters, and mixtures thereof may generally be used in minor proportions. Furthermore, coloring materials such as dyes and perfumes may be used, if desired. The amount of such adjuvants would range from 0 to about 20 percent by weight and preferably from about 1.0 to 10.0 percent by weight.

The following examples are included to further illustrate the present invention. Unless otherwise stated, throughout the application all parts and percentages are by weight and all temperatures are in degrees centigrade.

EXAMPLE 1

A concentrate is prepared from 20 parts of a polyoxyethylene-polyoxybutylene block copolymer of the type shown in formula (D) above, designated herein as copolymer #1, having a polyoxybutylene hydrophobe molecular weight of 5000 and containing oxyethylene groups in the amount of 70 percent of the total copolymer weight, 3 parts glycerine and 77 parts water. Fifty-two parts of this gel concentrate and 6 parts of isopropanol are placed in an aerosol container. Thirty-five parts by weight of dimethylether propellant is then added through the valve. The contents are shaken and sprayed onto a patch of human skin.

A thin film forms initially after which the dimethylether and isopropanol evaporate forming a coating on the skin. This becomes a foaming gel as the solvent and propellant evaporate.

EXAMPLE 2

A solution is prepared comprising 15.0 parts of a polyoxybutylene-polyoxyethylene copolymer, 3 parts of methylethylether, 0.1 part of neomycin and 81.9 parts of water.

One hundred parts of the above liquid are placed in an aerosol container, the container is pressurized and sealed with a valve and 50 parts of a propellant, namely dimethylether, added through the valve. The contents are shaken and sprayed onto a patch of human skin. A thin film forms initially after which the dimethylether and ethylmethylether evaporate whereby a foamy gel forms on the surface.

The polyoxyethylene-polyoxybutylene copolymer employed, designated herein as copolymer #2, is a polyoxyethylene adduct of a polyoxybutylene hydrophobic base having a molecular weight of said base of about 3000 and wherein the oxyethylene content is about 80 percent of the total weight of the molecule. The polyoxybutylene hydrophobic base is prepared by reacting 1,2-butylene oxide with a 1,4-butanediol initiator.

EXAMPLE 3

Example 2 is repeated using 100 parts of a liquid composition comprising 20.0 parts of copolymer #2, 5.0 parts of isopropyl alcohol, 1.0 part silver nitrate, 4.0 parts propylene glycol, and 70.0 parts water. Fifty parts of carbon dioxide were added to the aerosol container through the valve. When this composition is sprayed from the aerosol container, a thin film forms after spraying on the forearm of a human. This became a foamy gel as the solvent evaporates.

EXAMPLE 4

Example 2 is repeated substituting for copolymer #2 a polyoxyethylene-polyoxybutylene copolymer, designated herein as copolymer #3, having a hydrophobe molecular weight of 2500 and wherein the oxyethylene groups constitute about 90 percent of the total copolymer weight. When this composition is sprayed from the aerosol container, a thin film forms after spraying on the forearm of a human. This became a foamy gel as the solvent evaporates.

EXAMPLE 5

Example 2 is repeated substituting for copolymer #2 a polyoxyethylene-polyoxybutylene copolymer, designated herein as copolymer #4, having a hydrophobe molecular weight of about 10,000 and containing oxyethylene groups in amount of about 60 percent of the total copolymer weight. When this composition is sprayed from the aerosol container, a thin film forms after spraying on the forearm of a human. This became a foamy gel as the solvent evaporates.

EXAMPLE 6

Example 3 is repeated with the exception that 10 parts by weight of aloe vera is employed in lieu of 1 part by weight of silver nitrate and 61 parts by weight water is employed in lieu of the 70 parts by weight. When this composition is sprayed from the aerosol container, a thin film forms after spraying on the forearm of a human. This became a foamy gel as the solvent evaporates.

EXAMPLE 7

Example 6 is repeated with the exception that 20 parts aloe vera is employed in lieu of 10 parts and 51 parts by weight of water in lieu of 61 parts by weight. When this composition is sprayed from the aerosol container, a thin film forms after spraying on the forearm of a human. This became a foamy gel as the solvent evaporates.

EXAMPLE 8

Example 2 is repeated with the exception that the liquid composition consists of 15.0 parts of copolymer #2, 5.0 parts of glycerine, 3.0 parts of silver nitrate, 2.0 parts of acetone and 75 parts of water. Fifty parts of methylene chloride propellant are subsequently added to the aerosol container. When this composition is sprayed from the aerosol container, a thin film forms after spraying on the forearm of a human. This became a foamy gel as the solvent evaporates.

EXAMPLES 9-13

Five solutions are made up from all the components, excluding the propellants, of each of the example compositions set forth below and placed in its individual aerosol container of the type set forth in Example 1. The container is pressurized and sealed with a valve and the respective propellant added through the valve. The contents when shaken and sprayed onto the face of an individual needing a shave provides good shaving characteristics without irritating the skin. The compositions are as follows:

Example 8

| Parts by Weight | |
|---|---|
| 16 | Copolymer #1 |
| 3 | Glycerine |
| 1 | Lauric Diethanolamide |
| 60 | Water |
| 20 | Dimethyl Ether (Propellant) |
| 100 | |

Example 9

| Parts by Weight | |
|---|---|
| 14 | Copolymer #2 |
| 5 | Ethyl Alcohol |
| 1 | Ceric sulfadiazine |
| 50 | Water |
| 30 | Isobutane (Propellant) |
| 100 | |

Example 10

| Parts by Weight | |
|---|---|
| 18 | Copolymer #1 |
| 2 | Isopropyl Myristate |
| 1 | Lanolin |
| 3 | Isopropyl Alcohol |
| 66 | Water |
| 10 | Pentane (Propellant) |
| 100 | |

Example 11

| Parts by Weight | |
|---|---|
| 20 | Copolymer #4 |
| 2 | Isopropyl Palmitate |
| 1 | Dimethyl Polysiloxane |
| 3 | Ethyl Alcohol |
| 50 | Water |
| 24 | Freon 115 Propellant |
| 100 | |

Example 12

| Parts by Weight | |
|---|---|
| 15 | Copolymer #1 |
| 3 | Glyceryl Stearate |
| 2 | Propylene Glycol |
| 60 | Water |
| 5 | Methyl Alcohol |
| 15 | Freon C-318 Propellant |
| 100 | |

EXAMPLE 13

A solution comprising 20 parts of copolymer #1, 4 parts of isopropanol, 2 parts of 150 molecular weight polyethylene glycol, 3 parts acetylated lanolin alcohol, 0.7 part of fragrance, 1 part of 90 molecular weight polyethylene glycol, 0.2 part D&C Yellow No. 10 dye, 0.1 part F.D.&C Blue No. 1 dye and 2 parts specialty denatured ethyl alcohol and 67.1 parts water is prepared.

One hundred parts of the above liquid are placed in an aerosol container. The container is pressurized and sealed with a valve and 50 parts of isobutane propellant added through the valve. The contents when shaken and sprayed onto the human face having a growth of beard forms a coating which becomes a foamy gel as the propellant evaporates. The beard is softened for shaving without irritating the skin.

The embodiments in which an exclusive privilege or property is claimed are defined as follows:

1. A pressurized composition in an aerosol container and adapted to form a spray upon release of pressure therefrom which composition is a liquid inside the container and forms a gel on contact with living tissue comprising by weight about 35 to 80 percent water, 10 to 25 percent polyoxyethylene-polyoxybutylene copolymer of the formula:

$$Y[(C_4H_8O)_n(C_2H_4O)_mH]_x$$

wherein Y is the residue of a water-soluble organic compound containing therein x active hydrogen atoms; n is an integer; x is an integer greater than 1; the value of n and x are such that the molecular weight of the oxybutylene groups is from about 1000 to 20,000; and the value of m is such that the oxyethylene groups constitute about 60 to 90 percent of the total weight of the compound, and about 3 to 50 percent propellant which is a solvent for the composition in said container or propellant which is not a solvent for said composition plus about 1 to 10 percent of a non-propellant volatile solvent.

2. A composition of matter comprising by weight about 35 to 80 percent water, about 3 to 50 percent propellant, about 1 to 10 percent non-propellant volatile solvent and about 10 to 25 percent polyoxyethylene-polyoxybutylene copolymer of the formula:

$$Y[(C_4H_8O)_n(C_2H_4O)_mH]_x$$

wherein Y is the residue of a water-soluble organic compound containing therein x active hydrogen atoms; n is an integer; x is an integer greater than 1; the value of n and x are such that the molecular weight of the oxybutylene groups is from about 1000 to 20,000; and the value of m is such that the oxyethylene groups constitute about 60 to 90 percent of the total weight of the compound.

3. The composition of claim 2 wherein Y is a butylene glycol whereby the resulting compounds have the structure $HO(C_2H_4O)_m(C_4H_8O)_n(C_2H_4O)_mH$ wherein n has a value such that the oxybutylene groups have a molecular weight of about 2000 to 10,000 and m has a value such that the oxyethylene groups constitute about 60 to 90 percent of the total weight of the compound.

4. The composition of claim 3 including about 0.05 to 20 percent of at least one skin treatment agent.

5. The composition of claim 4 including about 1.0 to 20 percent of at least one adjuvant.

6. The composition of claim 5 wherein said composition is a burn treatment composition.

7. The composition of claim 5 wherein said composition is a shaving cream.

8. The composition of matter comprising by weight about 35 to 80 percent water, about 3 to 50 percent propellant which is a solvent, 0 to about 10 percent of a non-propellant volatile solvent and 10 to 25 percent polyoxyethylene-polyoxybutylene copolymer of the formula:

$$Y[(C_4H_8O)_n(C_2H_4O)_mH]_x$$

wherein Y is the residue of a water-soluble organic compound containing therein x active hydrogen atoms; n is an integer; x is an integer greater than 1; the value of n and x are such that the molecular weight of the oxybutylene groups is from about 1000 to 20,000; and the value of m is such that the oxyethylene groups constitute about 60 to 90 percent of the total weight of the compound.

9. The composition of claim 8 wherein Y is a butylene glycol whereby the resulting compounds have the structure $HO(C_2H_4O)_m(C_4H_8O)_n(C_2H_4O)_mH$ wherein n has a value such that the oxybutylene groups have a molecular weight of about 2000 to 10,000 and m has a value such that the oxyethylene groups constitute about 60 to 90 percent of the total weight of the compound.

10. The composition of claim 9 including about 0.05 to 10 percent of at least one skin treatment agent.

11. The composition of claim 10 including about 1.0 to 20 percent of at least one adjuvant.

12. The composition of claim 11 wherein said composition is a burn treatment composition.

13. The composition of claim 11 wherein said composition is a shaving cream.

14. A process for treating living skin comprising subjecting a gel composition to an elevated pressure in an aerosol container whereby said gel composition is a liquid, spraying said composition onto living skin, whereby a gel is formed on contact therewith, said composition comprising by weight about 35 to 80 percent water, about 10 to 25 percent of a polyoxyethylene-polyoxybutylene copolymer of the formula $$Y[(C_4H_8O)_n(C_2H_4O)_mH]_x$$

wherein Y is the residue of a water-soluble organic compound containing therein x active hydrogen atoms; n is an integer; x is an integer greater than 1; the value of n and x are such that the molecular weight of the oxybutylene groups is from about 1000 to 20,000; and the value of m is such that the oxyethylene groups constitute about 60 to 90 percent of the total weight of the compound, and about 3 to 50 percent propellant which is a solvent for the composition in said container or propellant which is not a solvent for said composition plus about 1 to 10 percent of a non-propellant volatile solvent.

15. An apparatus for treating skin comprising an aerosol container adapted to hold a material under pressure, a gel composition provided inside said container which is liquid when under the pressure normally found inside an aerosol container and which gels on contact with living skin at atmospheric pressure, a valve adapted to close off or release the liquid under pressure in the form of a spray, said gel composition comprising by weight abut 35 to 80 percent water, and 10 to 25 percent polyoxethylene-polyoxybutylene copolymer of the formula:

$$Y[(C_4H_8O)_n(C_2H_4O)_mH]_x$$

wherein Y is the residue of a water-soluble organic compound containing therein x active hydrogen atoms; n is an integer; x is an integer greater than 1; the value of n and x are such that the molecular weight of the oxybutylene groups is from about 1000 to 20,000; and the value of m is such that the oxyethylene groups constitute about 60 to 90 percent of the total weight of the compound, and about 3 to 50 percent propellant which is a solvent for the composition in said container or propellant which is not a solvent for said composition plus about 1 to 10 percent of a non-propellant volatile solvent.

* * * * *